(12) United States Patent
Fletcher et al.

(10) Patent No.: US 9,724,690 B2
(45) Date of Patent: Aug. 8, 2017

(54) BLOOD COLLECTION DEVICE, METHOD, AND SYSTEM FOR USING THE SAME

(75) Inventors: Gary D. Fletcher, Sparta, NJ (US); Sol F. Green, North Woodmere, NY (US); Myriam Lopez, Cliffside Park, NJ (US); Robert J. Losada, Astoria, NY (US); Dimitrios Manoussakis, Wyckoff, NJ (US); C. Mark Newby, Tuxedo, NY (US); Girish Parmar, Easton, PA (US); Paul R. Soskey, Neshanic Station, NJ (US); Timothy A. Stevens, Warwick, NY (US); Yuguang Wu, Montvale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1381 days.

(21) Appl. No.: 12/278,658

(22) PCT Filed: Feb. 8, 2007

(86) PCT No.: PCT/US2007/003438
§ 371 (c)(1),
(2), (4) Date: Dec. 31, 2008

(87) PCT Pub. No.: WO2007/092586
PCT Pub. Date: Aug. 16, 2007

(65) Prior Publication Data
US 2009/0130646 A1    May 21, 2009

Related U.S. Application Data

(60) Provisional application No. 60/771,923, filed on Feb. 8, 2006.

(51) Int. Cl.
*A61J 1/06* (2006.01)
*B01L 3/00* (2006.01)
(Continued)

(52) U.S. Cl.
CPC ............. *B01L 3/508* (2013.01); *B01L 3/5082* (2013.01); *B01L 3/50825* (2013.01); *G09F 3/00* (2013.01);
(Continued)

(58) Field of Classification Search
CPC .. B01L 3/50; B01L 3/502; B01L 3/508; B01L 2300/0861; B01L 2300/0864; G01N 35/10; G01N 35/1095
(Continued)

(56) References Cited

U.S. PATENT DOCUMENTS 3,266,298 A    8/1966   Whitehead et al.
3,482,082 A    12/1969  Isreeli
(Continued)

FOREIGN PATENT DOCUMENTS

EP    510615 A1    4/1992
EP    0486059 A1   5/1992
(Continued)

*Primary Examiner* — Jill Warden
*Assistant Examiner* — Dwayne K Handy
(74) *Attorney, Agent, or Firm* — The Webb Law Firm

(57) ABSTRACT

Disclosed is a fluid collection device wherein multiple, individual samples of fluid can be collected simultaneously. The device includes a chamber and an adapter which substantially and simultaneously distributes the blood to individual chambers with chamber specific additives. Also included is a system for using the blood collection device, preferably within a diagnostic testing laboratory.

6 Claims, 7 Drawing Sheets

(51) Int. Cl.
  *G09F 3/00*    (2006.01)
  *G01N 31/22*   (2006.01)
  *G01N 35/00*   (2006.01)
  *G09F 3/02*    (2006.01)

(52) U.S. Cl.
  CPC ... *B01L 2300/021* (2013.01); *B01L 2300/024* (2013.01); *B01L 2300/046* (2013.01); *B01L 2300/0663* (2013.01); *G01N 31/229* (2013.01); *G01N 2035/00861* (2013.01); *G09F 2003/0211* (2013.01); *G09F 2003/0272* (2013.01)

(58) Field of Classification Search
  USPC .................. 422/501, 544, 554, 559, 547
  See application file for complete search history.

(56) References Cited

U.S. PATENT DOCUMENTS

| | | | |
|---|---|---|---|
| 3,553,041 A | 1/1971 | Von Hofe | |
| 3,619,568 A | 11/1971 | Taplin | |
| 3,653,176 A | 4/1972 | Gess | |
| 3,656,473 A | 4/1972 | Sodickson et al. | |
| 3,843,440 A | 10/1974 | Davies | |
| 3,898,433 A | 8/1975 | Sallet | |
| 3,985,605 A | 10/1976 | Treiber et al. | |
| 4,292,916 A | 10/1981 | Bradley et al. | |
| 4,589,141 A | 5/1986 | Christian et al. | |
| 4,626,314 A | 12/1986 | Wesley | |
| 4,654,127 A | 3/1987 | Baker et al. | |
| 4,828,716 A | 5/1989 | McEwen et al. | |
| 5,025,798 A | 6/1991 | Schindele | |
| 5,119,830 A | 6/1992 | Davis | |
| 5,143,084 A * | 9/1992 | Macemon et al. | 600/584 |
| 5,145,565 A | 9/1992 | Kater et al. | |
| 5,150,795 A | 9/1992 | Nakayama | |
| 5,220,302 A * | 6/1993 | Nunnally et al. | 335/301 |
| 5,230,429 A | 7/1993 | Etheredge, III | |
| 5,296,375 A * | 3/1994 | Kricka et al. | 435/2 |
| 5,401,110 A | 3/1995 | Neeley | |
| 5,504,011 A * | 4/1996 | Gavin et al. | 422/73 |
| 5,633,835 A | 5/1997 | Haas et al. | |
| 5,688,361 A | 11/1997 | Itoh | |
| 5,743,861 A * | 4/1998 | Columbus et al. | 600/577 |
| 5,971,941 A | 10/1999 | Simons et al. | |
| 6,017,318 A | 1/2000 | Gauthier et al. | |
| 6,319,469 B1 * | 11/2001 | Mian et al. | 422/64 |
| 6,335,692 B1 | 1/2002 | Compton | |
| 6,373,786 B1 | 4/2002 | Kagan et al. | |
| 6,391,262 B1 | 5/2002 | Brinton et al. | |
| 6,533,015 B1 | 3/2003 | Moore | |
| 7,687,031 B2 | 3/2010 | Yamagata et al. | |
| 2003/0235119 A1 | 12/2003 | Wien et al. | |
| 2004/0171168 A1 | 9/2004 | Itoh | |
| 2004/0176704 A1 | 9/2004 | Stevens | |
| 2004/0257918 A1 | 12/2004 | Ribi | |
| 2005/0286350 A1 | 12/2005 | Wien | |

FOREIGN PATENT DOCUMENTS

| | | |
|---|---|---|
| EP | 0992287 A2 | 4/2000 |
| EP | 1004359 A2 | 5/2000 |
| JP | 1-156667 A | 6/1989 |
| JP | 3041365 A2 | 2/1991 |
| JP | 03-63570 | 3/1991 |
| JP | 4-63484 U | 5/1992 |
| JP | 05-95936 A | 4/1993 |
| JP | 5097133 A | 4/1993 |
| JP | 5-71792 U | 9/1993 |
| JP | 6-59937 | 8/1994 |
| JP | 07-167716 A | 7/1995 |
| JP | 9-504608 A | 5/1997 |
| JP | 9-236608 A | 9/1997 |
| JP | 2002-82120 A | 3/2002 |
| JP | 2002-102210 A | 4/2002 |
| JP | 2002-243734 A | 8/2002 |
| JP | 2003-004875 A | 1/2003 |
| JP | 2004-121704 A | 4/2004 |
| JP | 2004-347376 A | 12/2004 |
| WO | 01/26993 A1 | 4/2001 |
| WO | 02/06904 A1 | 1/2002 |
| WO | 2005/116632 A2 | 12/2005 |

\* cited by examiner

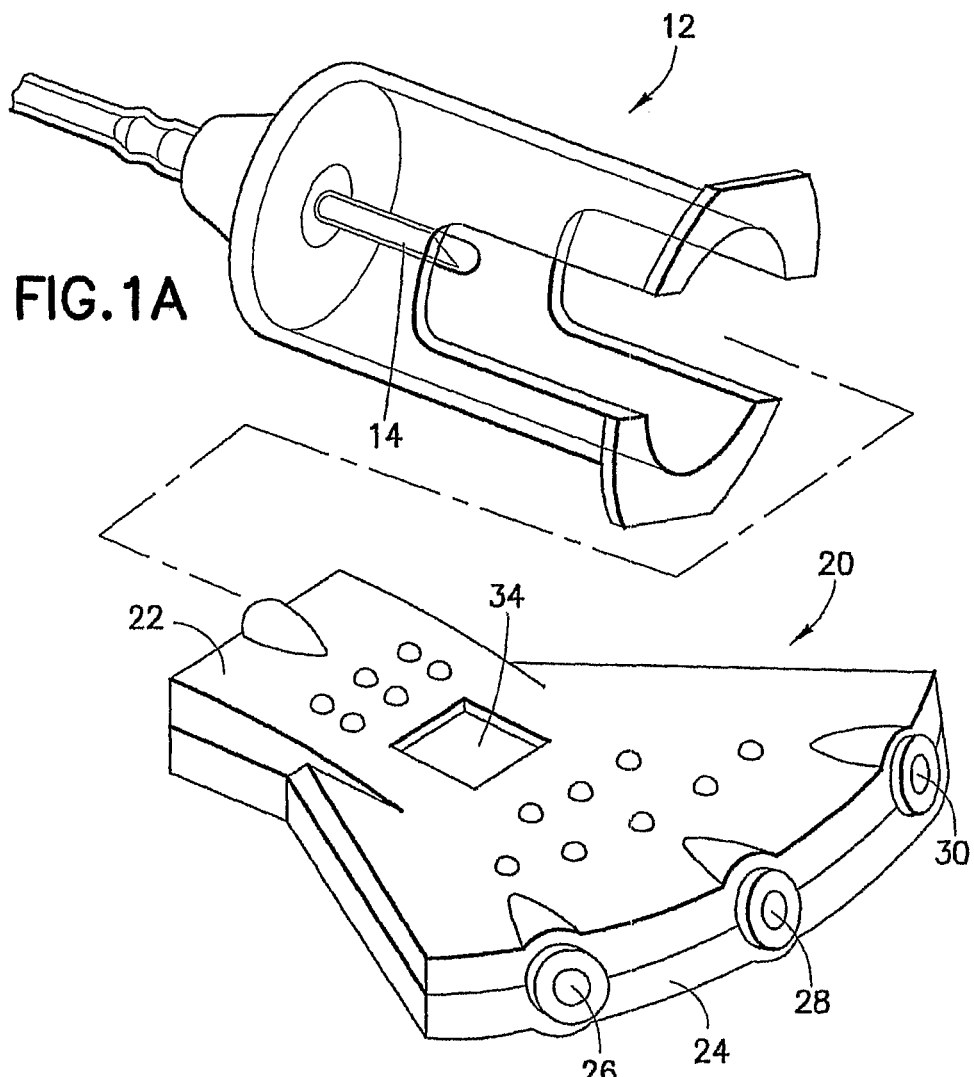
FIG.1A
FIG.1B
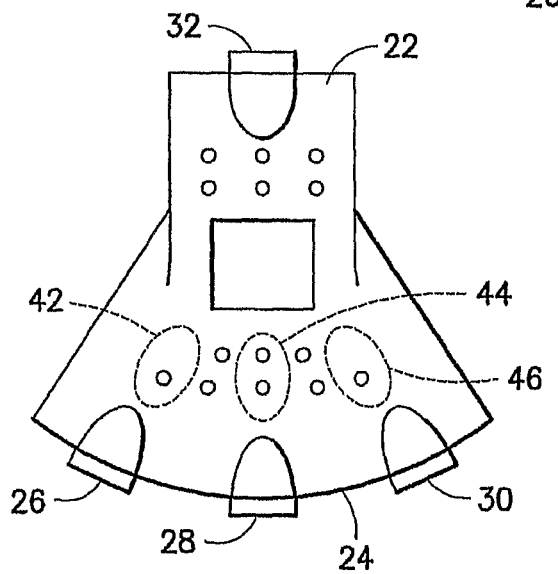
FIG.1C

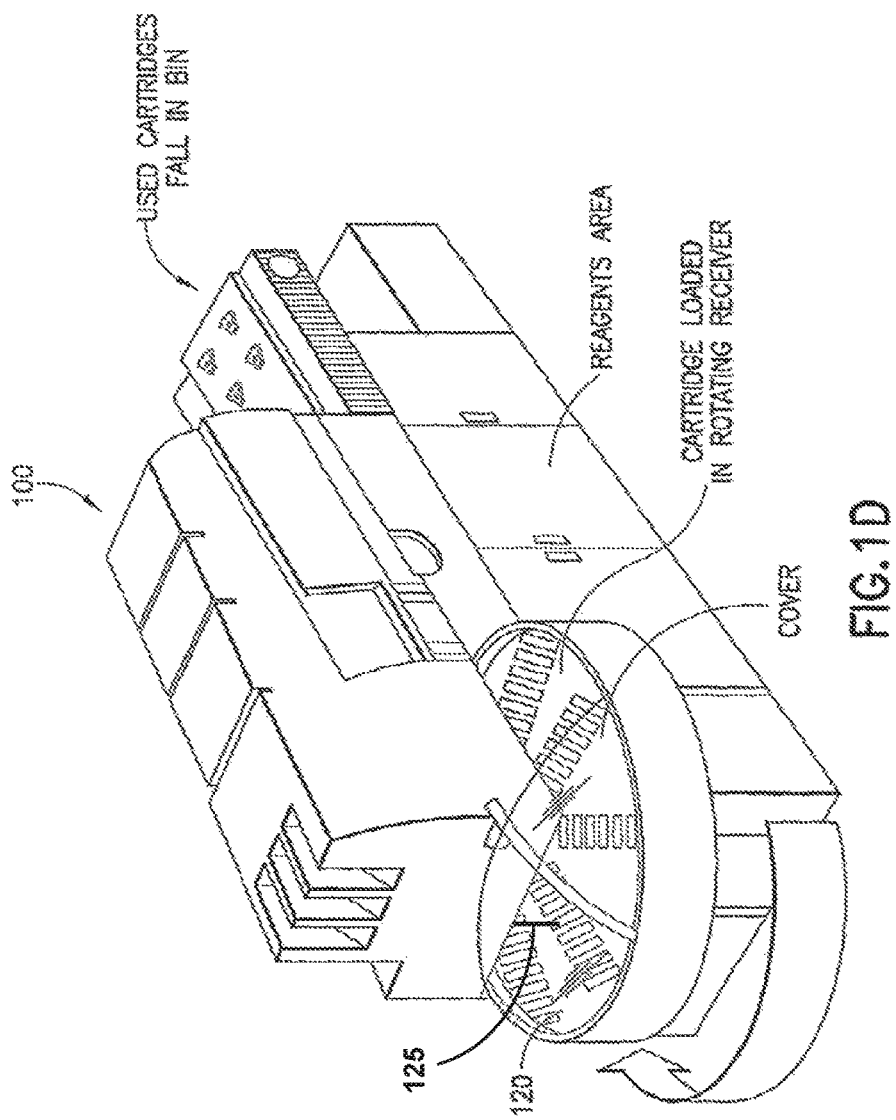

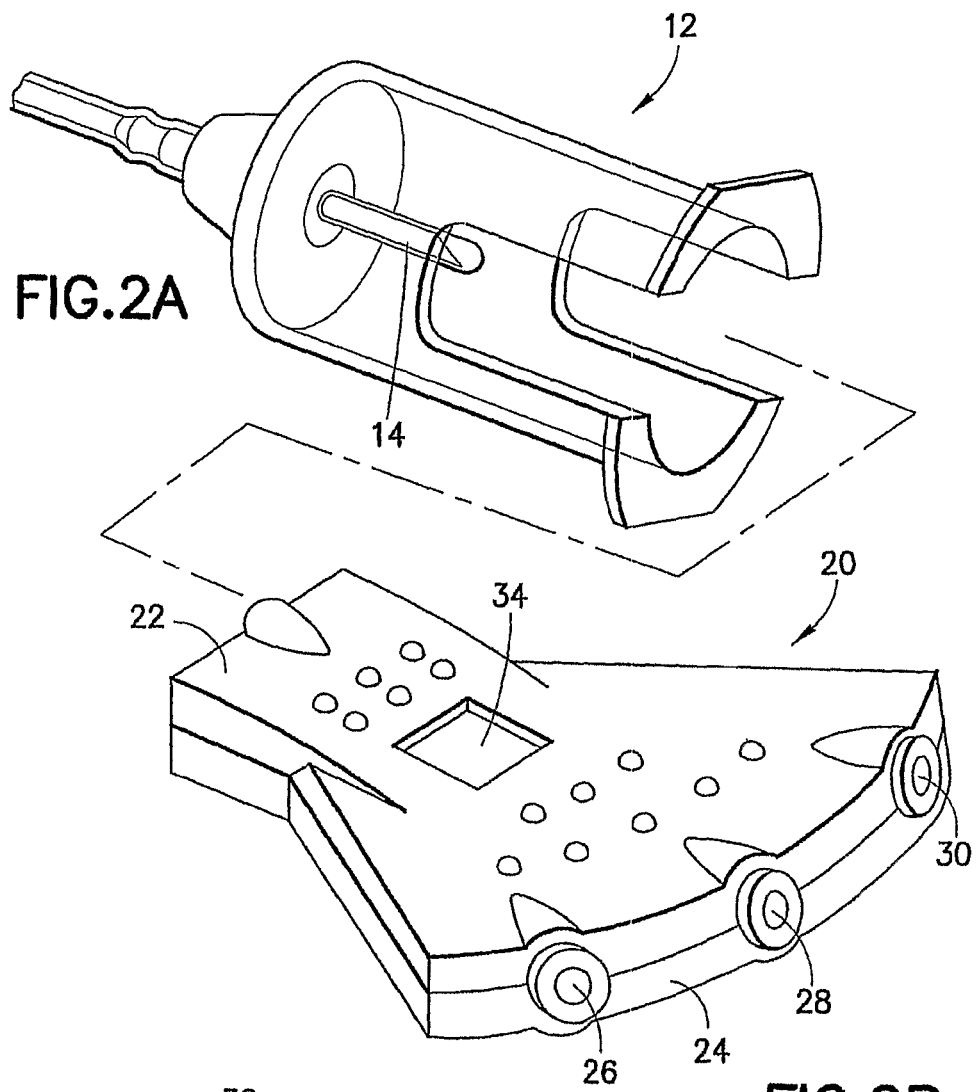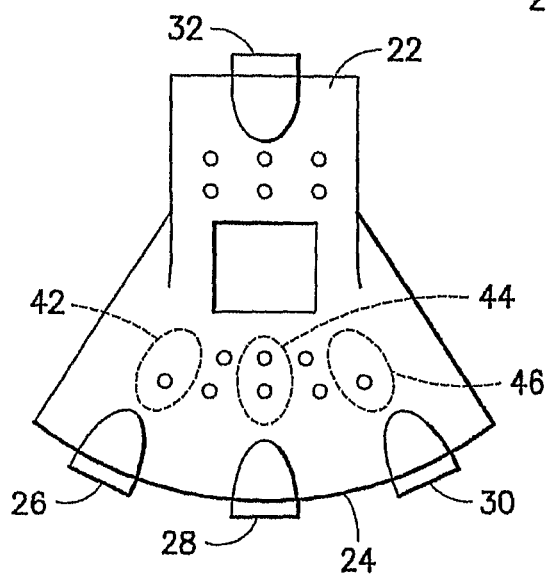

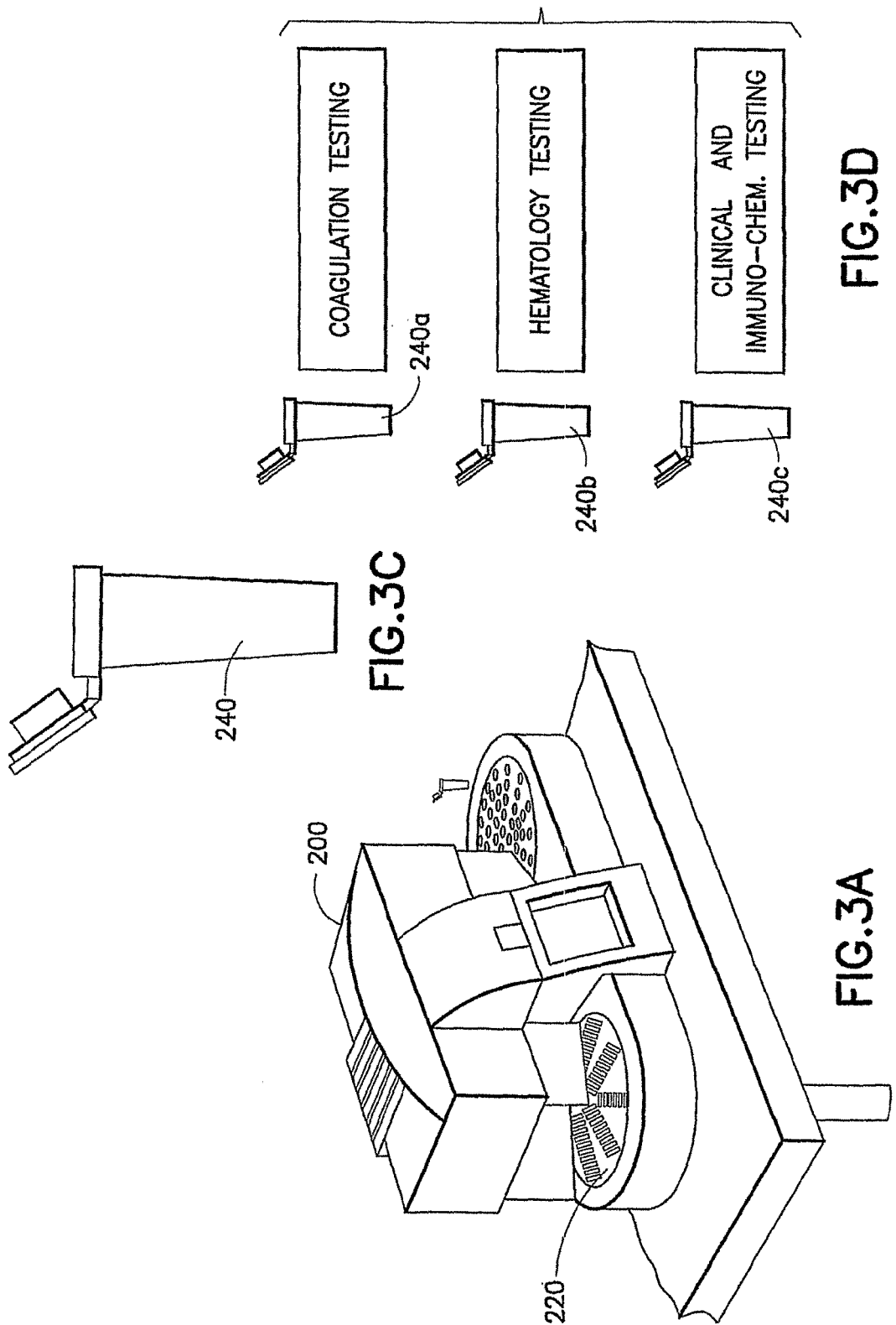

BLOOD COLLECTION DEVICE, METHOD, AND SYSTEM FOR USING THE SAME

FIELD OF THE INVENTION

This invention relates to body fluid collection devices, particularly for the collection of whole blood. More particularly, the invention relates to fluid collection devices wherein multiple, individual samples of fluid from the same source can be withdrawn simultaneously.

BACKGROUND OF INVENTION

U.S. Pat. No. 5,743,861 to Columbus et al. (herein incorporated by reference) discloses a cylindrical device which resembles a conventional blood collection tube. Improvements, of course, are always desired.

SUMMARY OF THE INVENTION

Improvements to the embodiments disclosed in U.S. Pat. No. 5,743,861 to Columbus et al. have been recognized. Provided is a blood collection device comprising a cartridge with a septum for interfacing with a fluid collection valve or port (i.e., blood collection needle, catheter port, blood collection set), a manifold in fluid communication with the piercing septum, a plurality of collection reservoirs in fluid communication with the manifold, each collection reservoir having additives and/or surface modifications and treatments that provide appropriate environmental conditions within the reservoir to achieve blood or sample stability for the test it is intended to be a part of. In certain embodiments, each reservoir would be designed such that a vacuum driving force would not be required to move the sample from the patient into the reservoirs.

Also disclosed is an analyzer that receives a cartridge and subsequently extracts from the cartridge from a plurality of collection reservoirs the aliquoted sample into individual sample vessels specific to the type of test (coagulation, hematology, clinical and/or immunochemistry).

Additional disclosure is directed to a blood analyzer wherein the analyzer receives a cartridge and within the analyzer is capable of performing coagulation, hematology, and clinical and/or immunochemistry analyses, especially from a single collection cartridge.

Further, a method for aliquoting biological fluids comprises the steps of: receiving a cartridge, the cartridge comprising multiple internal chambers, the content and surfaces of the chambers specific for at least two types of samples, wherein the samples are chosen from the group consisting of coagulation, hematology, immunochemistry, and clinical chemistry; and aliquoting from at least two of the chambers at least a portion of biological fluid temporarily residing in each chamber to at least one unique aliquot tube per chamber. An indicium may exist on the cartridge, wherein the indicium is interrogated by a scanning element prior to aliquoting. For example, the indicium may be a 1 dimensional or 2 dimensional bar code.

DESCRIPTION OF THE FIGURES

FIG. 1A shows a perspective view of a holder that relates to an embodiment of the invention.

FIG. 1B shows a perspective view of a cartridge that relates to an embodiment of the invention.

FIG. 1C shows a plan view of the cartridge depicted in FIG. 1B.

FIG. 1D shows a perspective view of an instrument that relates to an embodiment of the invention.

FIG. 2A shows a perspective view of a holder that relates to an embodiment of the invention.

FIG. 2B shows a perspective view of a cartridge that relates to an embodiment of the invention.

FIG. 2C shows a plan view of the cartridge depicted in FIG. 1B.

FIG. 3A shows a perspective view of an instrument that relates to an embodiment of the invention.

FIG. 3C shows a side view of a transport vessel that relates to the present invention.

FIG. 3D shows a side view of test specific vessels that relate to the present invention.

DETAILED DESCRIPTION

Figure 3B:
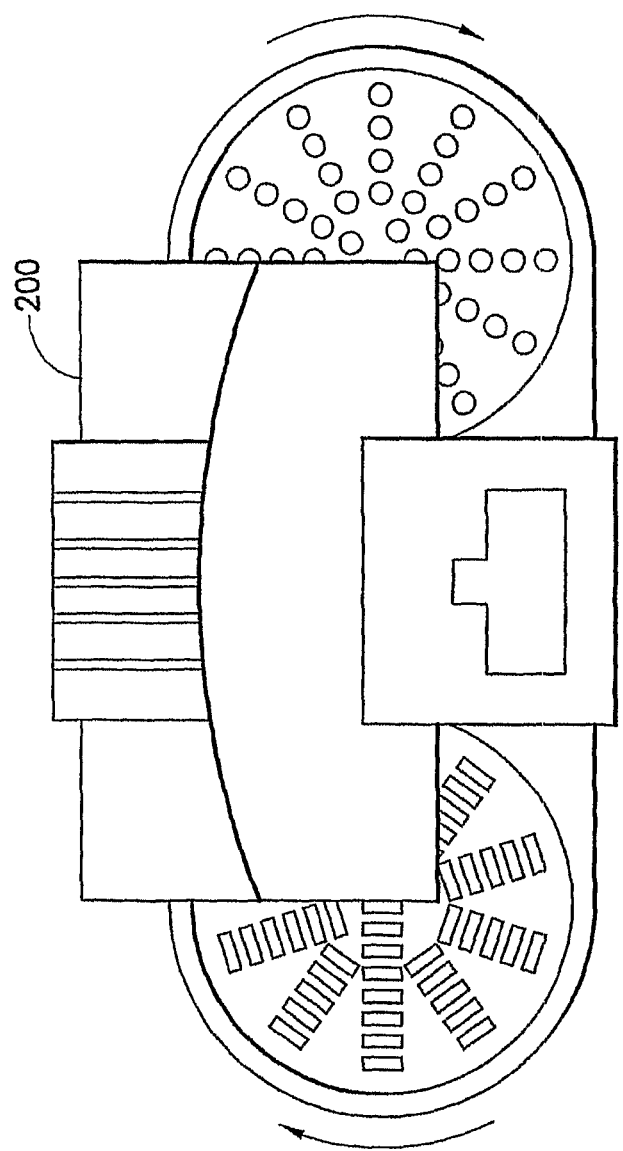
FIG. 3B shows a plan view of the cartridge depicted in FIG. 3A.

Described herein is a blood collection device for collecting and introducing in parallel, patient venous blood into a sealed multi-chambered cartridge 20, while preventing cross-contamination between the chambers. Because each chamber is isolated from the others, each chamber may contain chemical reagents or additives, which, in conventional evacuated tubes, would require separate tubes. The blood collection device of the invention allows simultaneous filing of each chamber by way of a distributor, which can be selectively placed into essentially simultaneous fluid communication with a plurality of the evacuated chambers. The blood is then able to pass from the source through the manifold and into the chambers.

The device of the invention is easy to use as it is compact and has a generally rectangular cross-sectional longitudinal shape and functions in a manner that closely resembles current blood collection technology with flexibility in fluid driving force. In particular, the blood collection device 20 is designed for use with a needle holder 10 and thus may be used when necessary or desired in conjunction with aliquot tubes or containers 240 for use with multiple test-specific analyzers (for instance, a coagulation aliquot tube or container 240a comprising citrate intended for coagulation testing; a hematology aliquot tube or container 240b comprising EDTA intended for hematology testing; or a clinical chemistry aliquot tube or container 240c comprising clot activator or enhancing surface to effect the intrinsic, extrinsic, or both intrinsic and extrinsic clotting cascades). By collecting and containing all of the desired blood samples in a single multi-chambered vessel, the number of disposables can be minimized and because multiple tubes and secondary containers may be eliminated, positive patient identification can be improved without requiring multiple container labeling for one patient sample. Furthermore, as discussed in more detail below, embodiments of the present invention employ features which may make it straightforward and inexpensive to manufacture despite the device's sophisticated capabilities.

The collection device 20 may be manufactured as components and assembled just prior to the taking of the patient sample or can be pre-assembled and ready-to-use. The device can be manufactured by utilizing any number of methods known in the art, however, the preferred method is one in which most parts are injection molded of a suitable plastic. Such plastics make the device light, unbreakable, and manufacturable at a modest cost. Furthermore, the collection device is preferably made of a biocompatible, U.S. Food and Drug Administration (FDA) approved plastic and metal components where desired that are compatible with the blood samples, chemical treatments, and analytical tests to be performed.

The overall internal cavities of each collection chamber in the blood collection device as well as the distributor aperture may be sealed, for example, with septums or self-healing seals. For instance, in a collection device 20 with multiple chambers 42, 44, and 46, septums 26, 28, and 30 respectively enable engagement between an aliquoting or extracting member 125 inserted into each chamber respectively through a seal. Such seals and septums are known in the art and allow penetration by a point, i.e., needle, such that upon withdrawal of the point, the seal substantially reseals to preclude fluid passage. Suitable materials for the seals are well known in the art and should be selected based on the intended use for the device such as biocompatibility, chemically inert, and compatible with any chemical reagents or treatments contained therein, be FDA approved, and suitable for use in automated instruments. Each aperture may be individually sealed after evacuation.

In operation, the blood collection device 20 may be used with a needle holder assembly 10 similar to that used for a conventional, evacuated blood collection tube (such as VACUTAINER™ marketed by Becton Dickinson and Company). The cartridge has a distal end 22 and a proximal end 24. After the needle is inserted into a vein, the penetrable septum 32 on the cartridge's distal end 22 is penetrated by the cannula 14 exposing the flow manifold in the cartridge to the blood source. A driving force in the chambers and manifold draws the blood through the cannula 14, the plenum/manifold, and into the respective chambers (42, 44, and 46) or reservoirs assisted by the venous pressure provided by the patient. When blood flow has ceased, the multi-chambered body/adapter unit may be removed from the needle holder assembly 10 as is the procedure with standard, evacuated collection tubes. The multi-chambered body may then be drawn away or removed completely from the adapter, allowing the self-healing septum 32 to reseal, thereby providing a plurality of chambers or reservoirs sealed with and containing blood.

As shown in FIGS. 1B, 1C, 2B, and 2C, the proximal end 22 of the cartridge 20 has at least one extraction port (26, 28, or 30) for each corresponding reservoir (42, 44, and 46 shown as dotted lines in FIG. 1C). The extraction ports may be employed to extract each sample of blood retained within the reservoir into an aliquoting instrument 200 shown in FIGS. 3A and 3B, wherein the instrument extracts the individual samples and transfers the samples into discreet, non-integral collection devices 240. This is shown in FIGS. 3A-3D. After the samples have been extracted from the cartridge 20 and segregated into different collection transport vessels 240, the vessels 240 may then be employed for analysis at a latter time in test-specific instruments.

Alternatively, the extraction port (26, 28, and 30) may be employed to extract each sample of blood retained within the reservoir into a multiple test instrument, wherein the instrument extracts the sample as needed and performs the appropriate analysis by whatever sample is extracted. In this embodiment shown in FIGS. 1A-1D, the instrument would likely need to identify and distinguish where within the cartridge 20 the sample for a certain type of test is located. In one embodiment, the instrument would be able to position the cartridge into the instrument and the geometry of the cartridge would enable only one orientation such that the instrument consistently recognizes which extraction port is needed to be accessed for specifically extracting the desired sample. In another embodiment, the instrument may scan an identifier 34 on the cartridge 20 (see FIG. 1B for identifier) to determine what extraction port is needed to be accessed. The above two embodiments are represented in FIG. 1B as well as 3A-3D.

In an embodiment of the invention, the internal cavity of the cartridge may employ a vacuum or partial pressure less than that of atmospheric pressure. The driving force of this vacuum assists in the delivery of blood from a patient's blood stream upon established fluid connection between the patient's blood and the cavity. To maintain vacuum, the sidewall and septums enclosing the cavity must be resistant to vacuum loss over a reasonable period of time, such as a year. In an embodiment of the invention, a foil seal covers the septum between the internal cavity of the cartridge such that once the foil seal is broken, the pressure between the cavity and the patient's blood attempt to equalize, thereby drawing the blood sample into the cavity and individual reservoirs.

As shown in FIG. 1, the assembled cartridge 20 accesses a needle 14 or port that is in fluid communication with a patient's vein. The distal end 22 of the cartridge 20 is shaped to allow for the cartridge to fit inside the proximal end of a holder 10. The holder 10 and cartridge 20 must be shaped in a manner to enable the cartridge to fill upon an establishment of connection. For instance, as shown in FIG. 1A holder 10 has conforming geometry such as a slot that conforms to the shape of the distal end 22 of cartridge 20. The driving force may be venous pressure, a partial vacuum inside the cartridge, capillary action, gravity, or other similar driving force such that the appropriate amount of fluid enters the reservoirs for appropriate filling. The proximal end 22 of the cartridge 20 may comprise at least one extraction port (26, 28, or 30) for each reservoir contained within the cartridge. For example a cartridge with three reservoirs (i.e., hematology reservoir 42, coagulation reservoir 44, and clinical chemistry reservoir 46) would have three extraction ports 26, 28, and 30 respectively.

Figure 4:
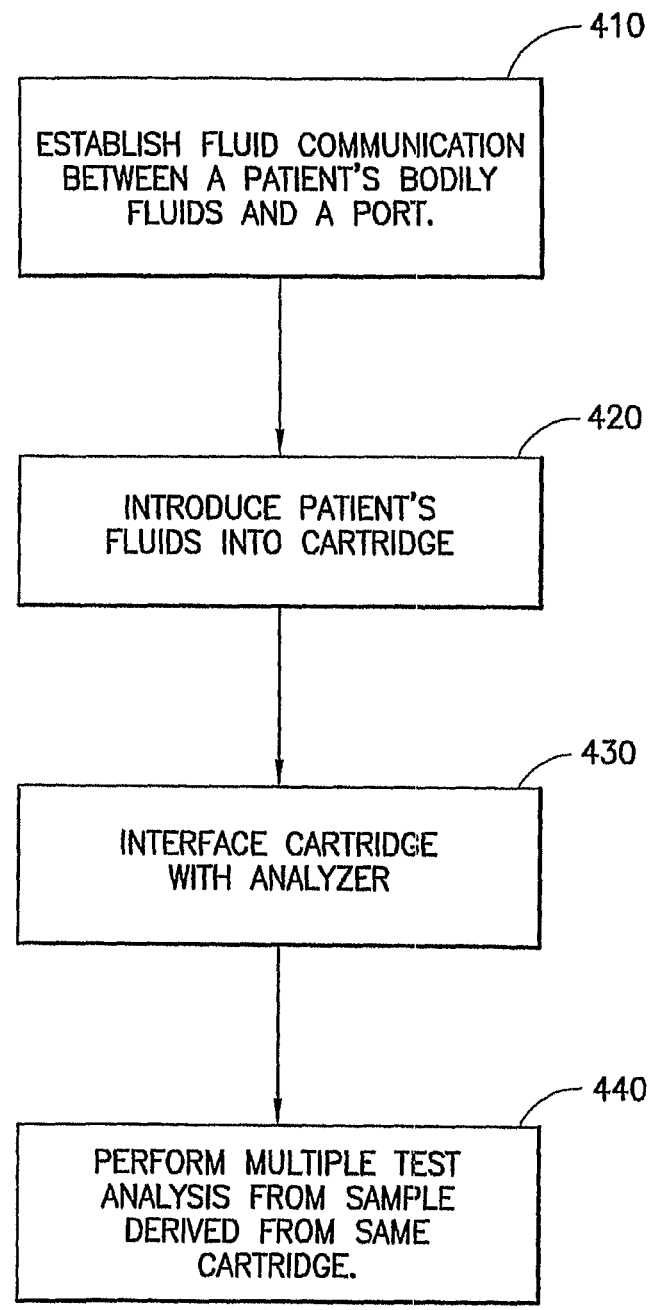
FIG. 4 shows a flow chart that relates to the present invention.

FIG. 4 provides a flow chart indicating the manner in which embodiments of the present invention may operate. Fluid communication is established between a patient's bodily fluids and a port of the cartridge (step 410). The fluid is introduced into the cartridge (step 420). The cartridge is interfaced with an analyzer (step 430). Finally, the analyzer performs multiple tests from different types of samples (hematology, coagulation, chemistry) within the same cartridge (step 440). For instance, the hematology sample within the cartridge may comprise EDTA within the chamber. The coagulation sample within the cartridge may comprise citrate. The chemistry portion of the cartridge may include clot activation surfaces commonly known in the art to promote the activation of either or both of the extrinsic or intrinsic clotting cascade.

Figure 5:
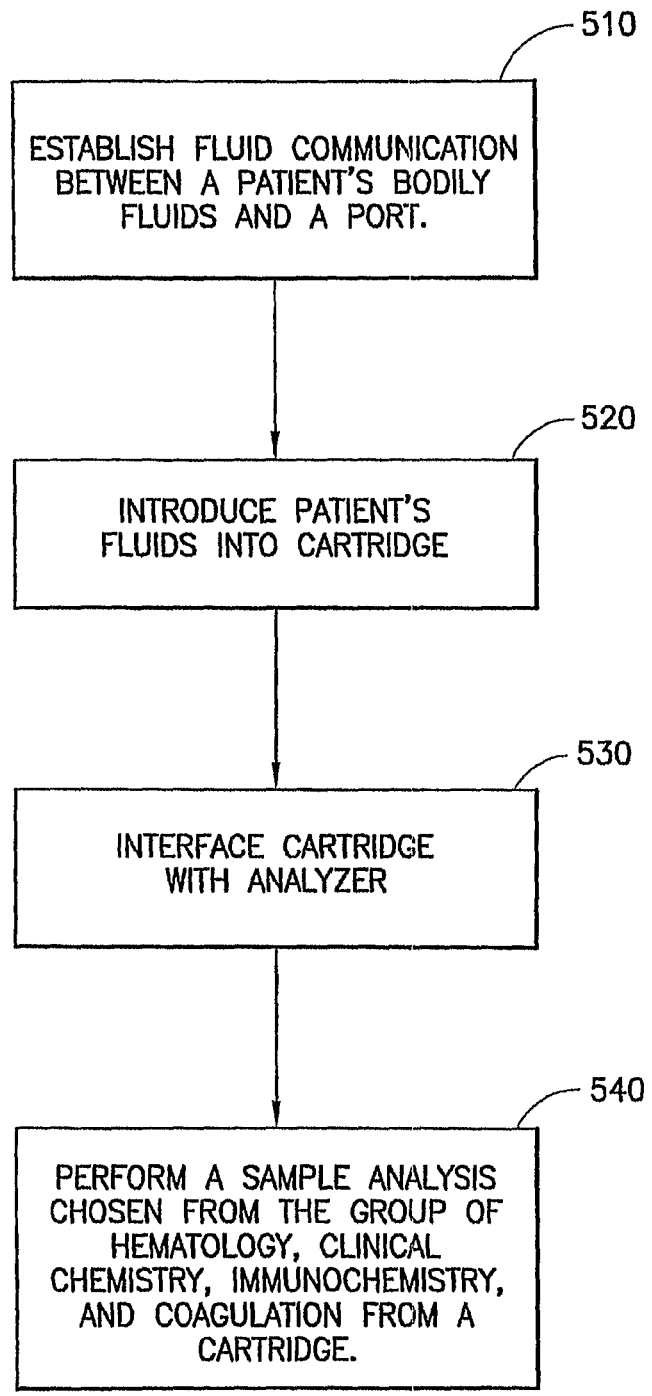
FIG. 5 shows a flow chart that relates to the present invention.

FIG. 5 provides a flow chart indicating the manner in which embodiments of the present invention may operate. For instance, in step 510, fluid communication is established between the patient's bodily fluids and a port. In step 520, the patient's fluids are introduced into the cartridge through one end of the cartridge. In step 530, the cartridge is interfaced with an analyzer (and/or aliquoter). Finally, in step 540, a sample analysis chosen from the group of hematology, clinical chemistry, immunochemistry, and coagulation is performed on the cartridge.

The present invention has been described with reference to preferred embodiments. One of skill in the art will readily appreciate that changes, alterations or modifications can be made to these embodiments without departing from the true scope and spirit of the invention.

What is claimed:

1. A system for accessing biological fluid for analytical testing, comprising:
   a cartridge including one inlet port, further comprising a plurality of extraction ports in fluid communication with the one inlet port, an internal chamber associated with each extraction port, wherein each of the internal chambers comprise an inlet capable of establishing fluid communication with the inlet port and an outlet capable of establishing fluid communication with the associated extraction port, and wherein the cartridge receives the biological fluid through the inlet port, the biological fluid received by the plurality of internal chambers; and
   an instrument for analytical testing configured to receive the cartridge, the instrument comprising at least one extraction member configured to be inserted into each of the extraction ports to extract the biological fluid from the internal chamber associated with the extraction port through which the at least one extraction member is inserted and into the at least one extraction member of the instrument.

2. The system of claim 1, wherein the instrument extracts the biological fluid from at least two of the internal chambers for performing at least two different analytical tests.

3. The system of claim 2, wherein the analytical tests are chosen from the group consisting of coagulation, hematology, immunochemistry, and clinical chemistry.

4. The system of claim 1, wherein the plurality of extraction ports comprise a plurality of separate extraction ports from the cartridge.

5. The system of claim 1, wherein, for each of the internal chambers, the inlet capable of establishing fluid communication with the inlet port comprises a different fluid path than a fluid path of the outlet capable of establishing fluid communication with the associated extraction port.

6. A system for accessing biological fluid for analytical testing, comprising:
   a cartridge including a single inlet port, further comprising a plurality of extraction ports, an internal chamber associated with each extraction port, wherein each of the internal chambers comprises an inlet capable of establishing fluid communication with the single inlet port and an outlet capable of establishing fluid communication with the associated extraction port, and wherein the cartridge receives the biological fluid through the single inlet port, the biological fluid received by the plurality of internal chambers; and
   an instrument for analytical testing configured to receive the cartridge, the instrument comprising at least one extraction member configured to be inserted into each of the extraction ports to extract the biological fluid from the internal chamber associated with the extraction port through which the at least one extraction member is inserted and into the at least one extraction member.

* * * * *